US 9,526,497 B2

(12) United States Patent
Cappola et al.

(10) Patent No.: US 9,526,497 B2
(45) Date of Patent: Dec. 27, 2016

(54) SURGICAL INSTRUMENT WITH ARTICULATION MECHANISM

(71) Applicant: Covidien LP, Mansfield, MA (US)

(72) Inventors: Kenneth M. Cappola, Monroe, CT (US); Frank Marini, Monroe, CT (US); Kenneth M. Horn, Middletown, CT (US)

(73) Assignee: Covidien LP, Mansfield, MA (US)

( * ) Notice: Subject to any disclaimer, the term of this patent is extended or adjusted under 35 U.S.C. 154(b) by 849 days.

(21) Appl. No.: 13/849,572

(22) Filed: Mar. 25, 2013

(65) Prior Publication Data

US 2013/0292448 A1 Nov. 7, 2013

Related U.S. Application Data

(60) Provisional application No. 61/643,389, filed on May 7, 2012.

(51) Int. Cl.
| | | |
|---|---|---|
| *A61B 17/00* | (2006.01) | |
| *A61B 17/03* | (2006.01) | |
| *A61B 17/068* | (2006.01) | |
| *A61B 17/072* | (2006.01) | |
| *A61B 17/29* | (2006.01) | |

(52) U.S. Cl.
CPC ....... *A61B 17/068* (2013.01); *A61B 17/07207* (2013.01); *A61B 2017/00367* (2013.01); *A61B 2017/2927* (2013.01); *A61B 2017/2929* (2013.01)

(58) Field of Classification Search
CPC .................. A61B 17/00367; A61B 2017/2929
USPC ........................................... 227/175.1–182.1
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |

(Continued)

FOREIGN PATENT DOCUMENTS

| | | |
|---|---|---|
| AU | 198654765 | 9/1986 |
| DE | 2744824 | 4/1978 |

(Continued)

OTHER PUBLICATIONS

European Search Report EP13166379.1 dated Sep. 4, 2013.

*Primary Examiner* — Gloria R Weeks
*Assistant Examiner* — Eyamindae Jallow

(57) ABSTRACT

A surgical instrument for surgically joining tissue is disclosed. The instrument comprises a handle assembly, an elongated portion, an end effector, and an articulation mechanism. The elongated portion extends distally from the handle assembly. The end effector is disposed adjacent a distal portion of the elongated portion. The articulation mechanism is disposed in mechanical cooperation with the end effector for articulating the end effector. The articulation mechanism comprises a lever, a knob, a plate and a lower clutch. The plate is disposed at least partially within a portion of the knob. The lower clutch is disposed in mechanical engagement with the plate. The plate is disposed at least partially between the lower clutch and the knob. The lower clutch is keyed to the plate to limit rotation therebetween. The lower clutch is keyed to the knob to limit rotation therebetween.

20 Claims, 14 Drawing Sheets

(56) References Cited

U.S. PATENT DOCUMENTS

| | | |
|---|---|---|
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |

(56) References Cited

U.S. PATENT DOCUMENTS

| | | |
|---|---|---|
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Gerbi et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |

(56) References Cited

U.S. PATENT DOCUMENTS

| | | |
|---|---|---|
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |

(56) References Cited

U.S. PATENT DOCUMENTS

| | | |
|---|---|---|
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |

(56) References Cited

U.S. PATENT DOCUMENTS

| | | |
|---|---|---|
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,576 B2 | 11/2011 | Cappola |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk et al. |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,267,300 B2 | 9/2012 | Boudreaux |
| 8,272,554 B2 | 9/2012 | Whitman et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0006434 A1 | 1/2005 | Wales et al. |
| 2005/0103819 A1 | 5/2005 | Racenet |
| 2005/0119669 A1 | 6/2005 | Demmy |
| 2005/0189397 A1 | 9/2005 | Jankowski |
| 2005/0216055 A1 | 9/2005 | Scirica et al. |
| 2006/0049229 A1 | 3/2006 | Milliman et al. |
| 2006/0180634 A1 | 8/2006 | Shelton, IV et al. |
| 2006/0289602 A1 | 12/2006 | Wales et al. |
| 2007/0027469 A1 | 2/2007 | Smith et al. |
| 2007/0073341 A1 | 3/2007 | Smith et al. |
| 2007/0084897 A1 | 4/2007 | Shelton, IV et al. |
| 2007/0084899 A1 | 4/2007 | Taylor |
| 2007/0102472 A1 | 5/2007 | Shelton, IV |
| 2007/0106317 A1 | 5/2007 | Shelton, IV |
| 2007/0119901 A1 | 5/2007 | Ehrenfels et al. |
| 2007/0145096 A1 | 6/2007 | Viola et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |

(56) References Cited

U.S. PATENT DOCUMENTS

| | | |
|---|---|---|
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296344 A1 | 12/2008 | Cropper et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2010/0012703 A1 | 1/2010 | Calabrese et al. |
| 2010/0012704 A1 | 1/2010 | Racenet et al. |
| 2010/0069942 A1 | 3/2010 | Shelton, IV et al. |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062211 A1 | 3/2011 | Ross et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |

(56) References Cited

FOREIGN PATENT DOCUMENTS

| | | |
|---|---|---|
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 2258281 A2 | 12/2010 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 6/1975 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89/10094 | 11/1989 |
| WO | WO 9210976 | 7/1992 |
| WO | WO 9308754 | 5/1993 |
| WO | WO 9314706 | 8/1993 |

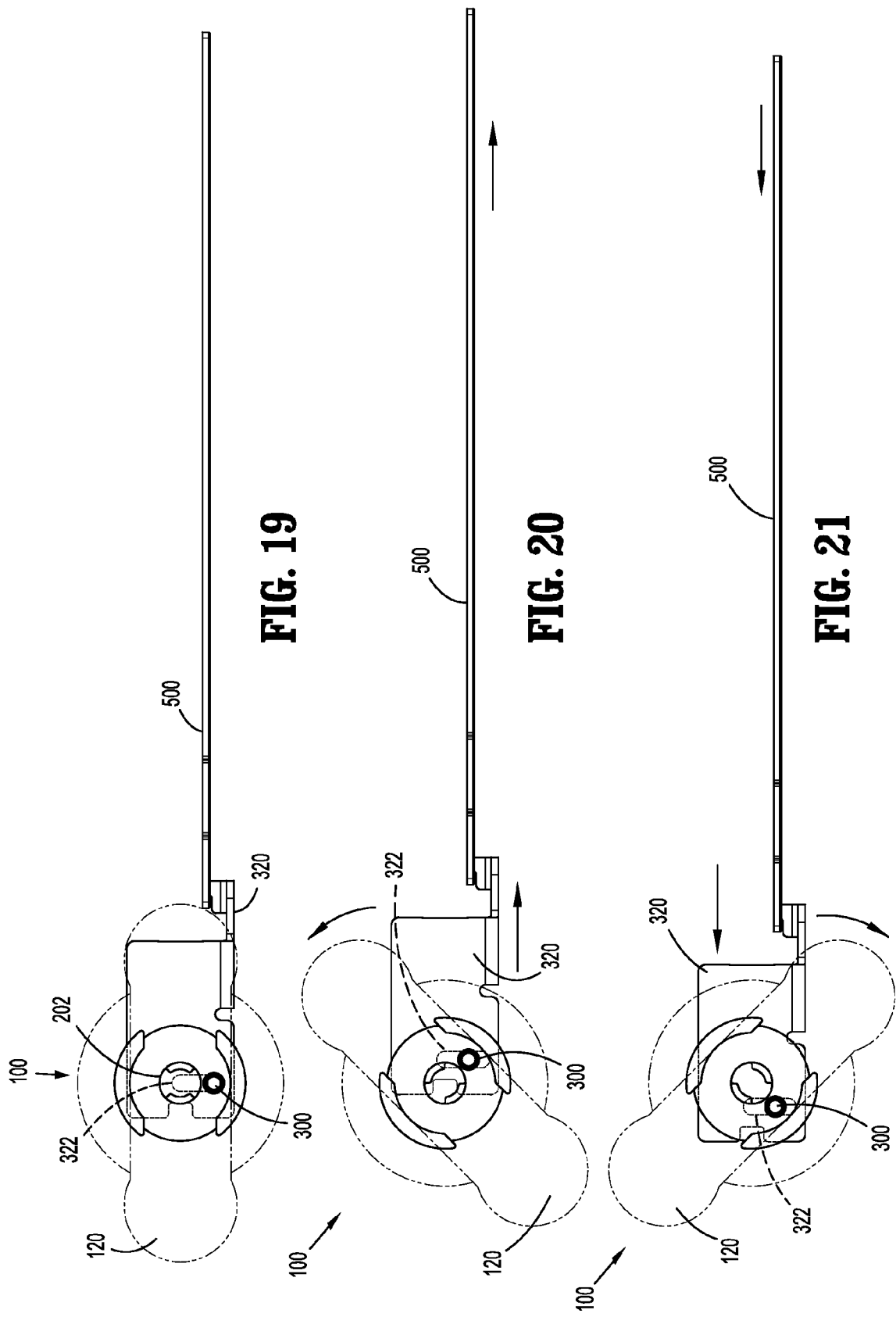

SURGICAL INSTRUMENT WITH ARTICULATION MECHANISM

CROSS-REFERENCE TO RELATED APPLICATIONS

This application claims the benefit of and priority to U.S. Provisional Patent Application No. 61/643,389, filed May 7, 2012, the entire disclosure of which is incorporated by reference herein.

BACKGROUND

1. Technical Field

The present disclosure relates generally to instruments for surgically joining tissue and, more specifically, to surgical instruments capable of articulation and articulation mechanisms for use therewith.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

SUMMARY

The present disclosure relates to a surgical instrument for surgically joining tissue. The instrument comprises a handle assembly, an elongated portion, an end effector, and an articulation mechanism. The elongated portion extends distally from the handle assembly. The end effector is disposed adjacent a distal portion of the elongated portion. The articulation mechanism is disposed in mechanical cooperation with the end effector for articulating the end effector. The articulation mechanism comprises a lever, a housing, a plate and a lower clutch. The plate is disposed at least partially within a portion of the housing. The lower clutch is disposed in mechanical engagement with the plate. The plate is disposed at least partially between the lower clutch and the housing. The lower clutch is keyed to the plate to limit rotation therebetween. The lower clutch is keyed to the housing to limit rotation therebetween.

In disclosed embodiments, the plate is rotatable with respect to the housing prior to engagement between the lower clutch and the plate.

In disclosed embodiments, the lower clutch is keyed to the plate via four keys.

In disclosed embodiments, the lower clutch is keyed to the housing via two keys. Here, it is disclosed that the two keys used to key the lower clutch to the housing are also used to key the lower clutch to the plate.

In disclosed embodiments, the articulation mechanism further comprises a cover disposed in contact with the lever, a biasing element disposed in mechanical cooperation with the cover, and an upper clutch disposed in mechanical cooperation with the lower clutch and in mechanical cooperation with the biasing element. Here, it is disclosed that the distance the upper clutch can move with respect to the housing due to compression of the biasing element is distance "a," a radial edge of the cover is spaced from the lever a distance "b," the lower clutch is keyed to the housing via at least one key, the key having a distance "c" disposed in the same direction as distances "a" and "b," and the distance "c" is greater than the distance "a" plus distance "b."

In disclosed embodiments, the articulation mechanism comprises a drive element disposed in mechanical cooperation with the housing. A shaft of the drive element extends through apertures of the plate and the lower clutch. The shaft is mechanically coupled to the lever. Here, it is disclosed that the articulation mechanism further comprises an articulation shaft disposed in mechanical cooperation with the drive element, such that rotation of the drive element causes translation of the articulation shaft along the first longitudinal axis.

The present disclosure also relates to an articulation mechanism for use with a surgical instrument. The articulation mechanism comprises a lever, a knob, a lower clutch disposed in mechanical cooperation with the knob, a cover disposed in contact with the lever, a biasing element disposed in mechanical cooperation with the cover, and an upper clutch disposed in mechanical cooperation with the lower clutch and in mechanical cooperation with the biasing element. The distance the upper clutch can move with respect to the knob due to compression of the biasing element is distance "a," a radial edge of the cover is spaced from the lever a distance "b," the lower clutch is keyed to the knob via at least one key, the key having a distance "c" disposed in the same direction as distances "a" and "b," and the distance "c" is greater than the distance "a" plus distance "b."

In disclosed embodiments, the articulation mechanism further comprises a plate disposed between the knob and the lower clutch. Here, it is disclosed that the lower clutch is keyed to the plate to limit rotation therebetween. It is further disclosed that the plate is rotatable with respect to the knob prior to engagement between the lower clutch and the plate. It is further disclosed that the lower clutch is keyed to the plate via four keys.

In disclosed embodiments, wherein the lower clutch is keyed to the knob via two keys. Here, it is disclosed that the articulation mechanism further comprises a plate disposed between the knob and the lower clutch. The two keys used to key the lower clutch to the knob are also used to key the lower clutch to the plate.

In disclosed embodiments, the articulation mechanism further comprises a drive element disposed in mechanical cooperation with the knob. A shaft of the drive element extends through an aperture of the plate, and the shaft is mechanically coupled to the lever. Here, it is disclosed that the articulation mechanism further comprises an articulation shaft disposed in mechanical cooperation with the drive element, such that rotation of the drive element causes longitudinal translation of the articulation shaft.

BRIEF DESCRIPTION OF FIGURES

Various embodiments of the presently disclosed surgical instrument are disclosed herein with reference to the drawings, wherein:

FIG. 19 is a schematic view of the articulation mechanism in a neutral position and an articulation shaft in a neutral position; and FIGS. 20 and 21 are schematic views of the articulation mechanism in rotated positions, and the articulation shaft in advanced and retracted positions.

DETAILED DESCRIPTION

Figure 1:
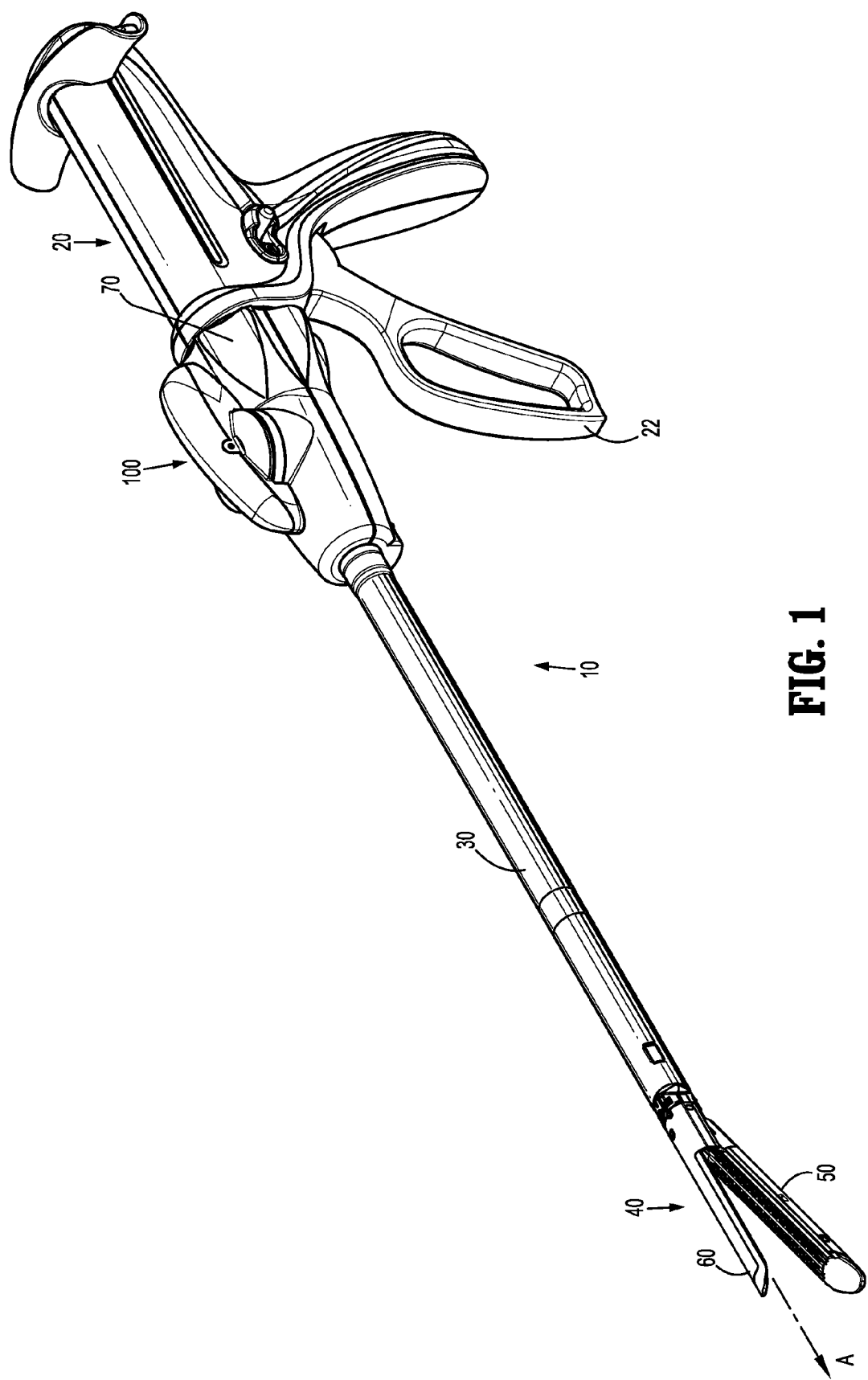
FIG. 1 is a perspective view of a surgical stapling instrument with its jaw members in a linear orientation in accordance with the present disclosure.

Embodiments of the presently disclosed surgical instrument, and articulation mechanism for use therewith, are described in detail with reference to the drawings, wherein like reference numerals designate corresponding elements in each of the several views. As is common in the art, the term 'proximal" refers to that part or component closer to the user or operator, e.g., surgeon or physician, while the term "distal" refers to that part or component farther away from the user.

A surgical stapling instrument of the present disclosure is indicated as reference numeral 10 in FIG. 1. An articulation mechanism for use with the surgical instrument is indicated as reference number 100 in the accompanying figures. The depicted surgical instrument fires staples, but it may be adapted to fire any other suitable fastener such as clips and two-part fasteners. Additionally, while the figures depict a linear fastener-applying surgical instrument, other types of endoscopic surgical instruments are encompassed by the present disclosure and are usable with the disclosed articulation assembly 100. For example, further details of endoscopic forceps are described in commonly-owned U.S. Patent Publication No. 2010/0179540 to Marczyk et al., and U.S. patent application Ser. No. 12/718,143 to Marczyk et al., the entire contents of each of which are hereby incorporated by reference herein. In another example, further details of a circular fastener-applying surgical instrument are described in commonly-owned U.S. Patent Publication No. 2009/0173767 to Milliman et al., the entire contents of which are hereby incorporated by reference herein.

Generally, surgical instrument 10 includes a handle assembly 20 including a movable handle 22, an endoscopic portion 30 extending distally from the handle assembly 20 and defining a longitudinal axis "A," and an end effector 40, including a cartridge 50 and an anvil 60, disposed adjacent a distal portion of the endoscopic portion 30. The movable handle 22 is actuatable (e.g., through successive strokes) to cause distal advancement of a drive rod, such that the drive rod engages a portion of a drive assembly, which forces at least a portion of the drive assembly to translate distally. (Further details of how actuation of movable handle 22 causes distal advancement of the drive rod are explained in U.S. Pat. No. 6,953,139 to Milliman et al., which is hereby incorporated by reference herein.) Distal movement of the drive rod, and in particular, a dynamic clamping member affixed thereto, causes an actuation sled to move distally through the cartridge 50, which causes cam wedges of the actuation sled to sequentially engage pushers to move pushers vertically within retention slots and eject fasteners towards the anvil 60. Subsequent to the ejection of fasteners from the retention slots (and into tissue), a cutting edge of the dynamic clamping member severs the fastened tissue as the cutting edge travels distally through a slot of the cartridge 50.

Additionally, a loading unit may be attachable to an elongated or endoscopic portion 30 of surgical instrument 10 of the present disclosure, e.g., to allow surgical instrument 10 to have greater versatility. The loading unit may be configured for a single use, and/or may be configured to be used more than once. Examples of loading units for use with a surgical stapling instrument are disclosed in commonly-owned U.S. Pat. No. 5,752,644 to Bolanos et al., the entire contents of which are hereby incorporated by reference herein. It is also contemplated that the articulation mechanism can be used in a surgical instrument that has a replaceable cartridge assembly in the jaws of the instrument.

Figure 1A:
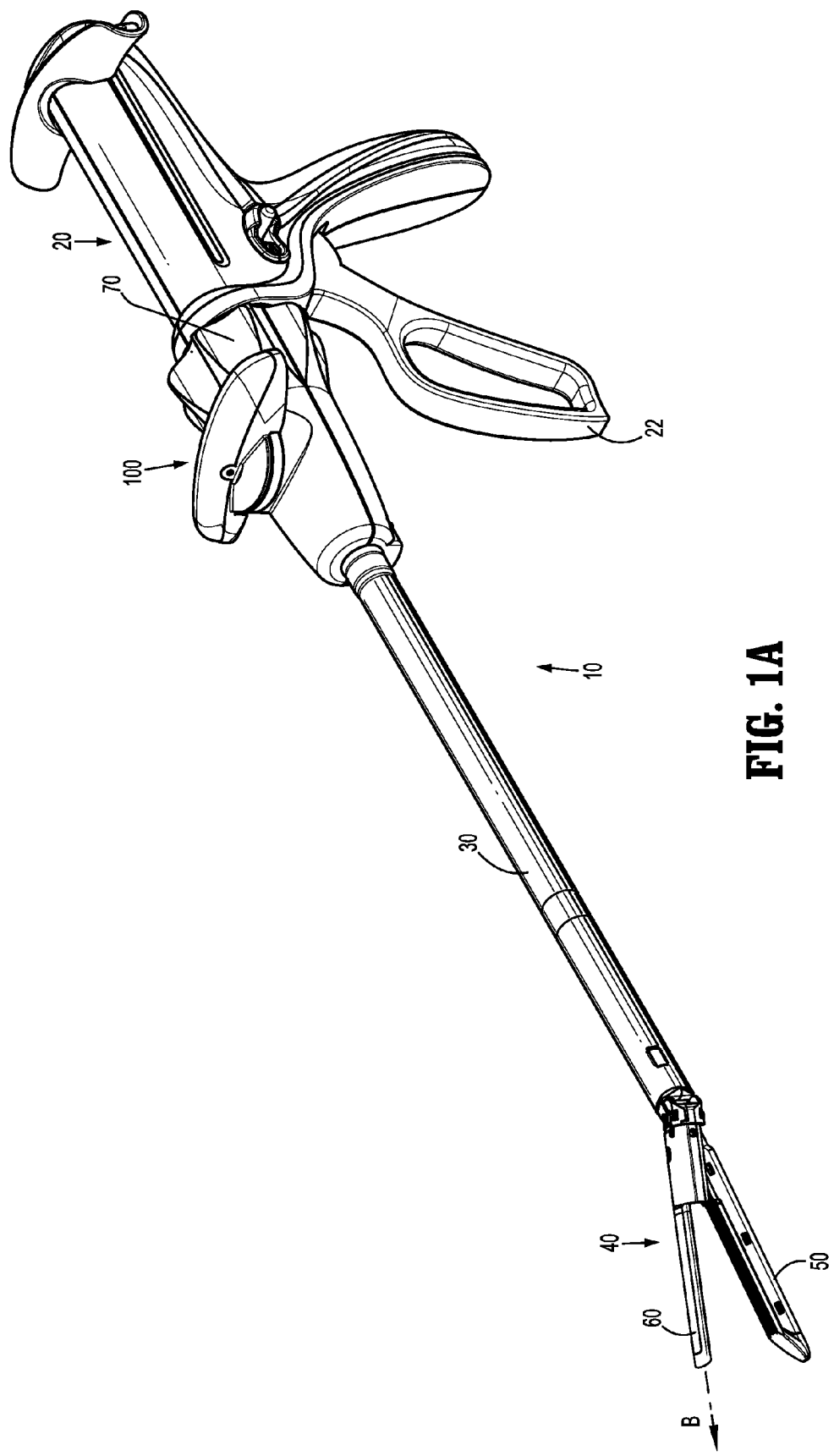
FIG. 1A is a perspective view of the surgical stapling instrument of FIG. 1, with its jaw member in an articulated orientation.
Figure 2:
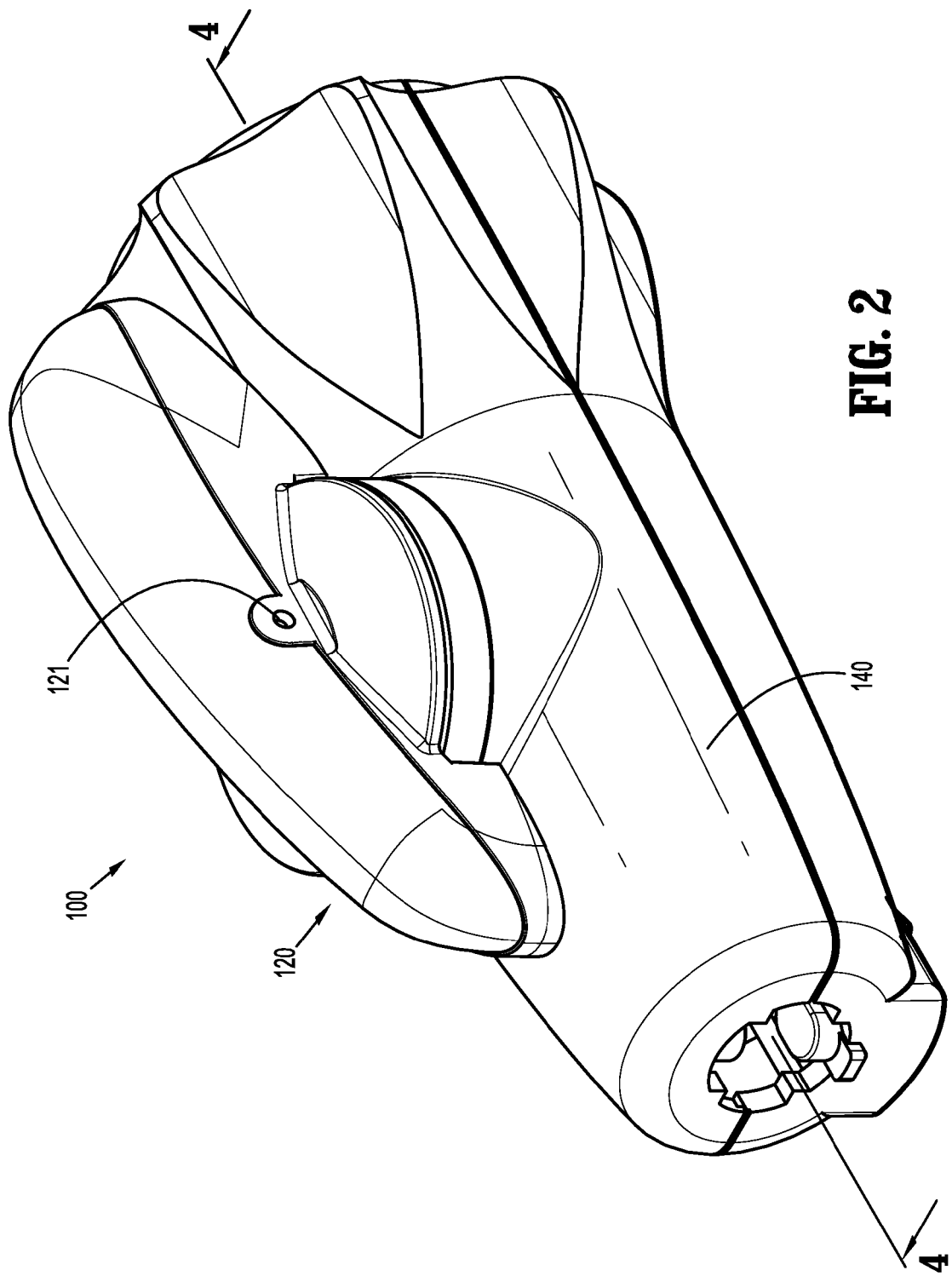
FIG. 2 is a perspective view of an articulation mechanism of the surgical stapling instrument of FIG. 1.

Surgical instrument 10 also includes an articulation mechanism 100 for articulating the jaw members (i.e., cartridge 50 and anvil 60) of end effector 40. In particular, the jaw members, which define an axis "B" (see FIG. 1B), are movable from between a first position where axis "B" is aligned with an axis "A" defined by endoscopic portion 30 (FIG. 1) and a second position where axis "B" is disposed at an angle with respect to axis "A" (FIG. 1A).

Articulation mechanism 100 is disposed in mechanical cooperation with handle assembly 20. In the illustrated embodiment, articulation mechanism 100 is disposed on a rotation mechanism 70 of surgical instrument 10, but it is envisioned that articulation mechanism 100 could be located on or adjacent another portion of handle assembly 20. Articulation mechanism 100 is used to longitudinally translate an articulation shaft 500 (FIGS. 19-21) with respect to handle assembly 20 to cause articulation of the jaw members of end effector 40.

Figure 3:
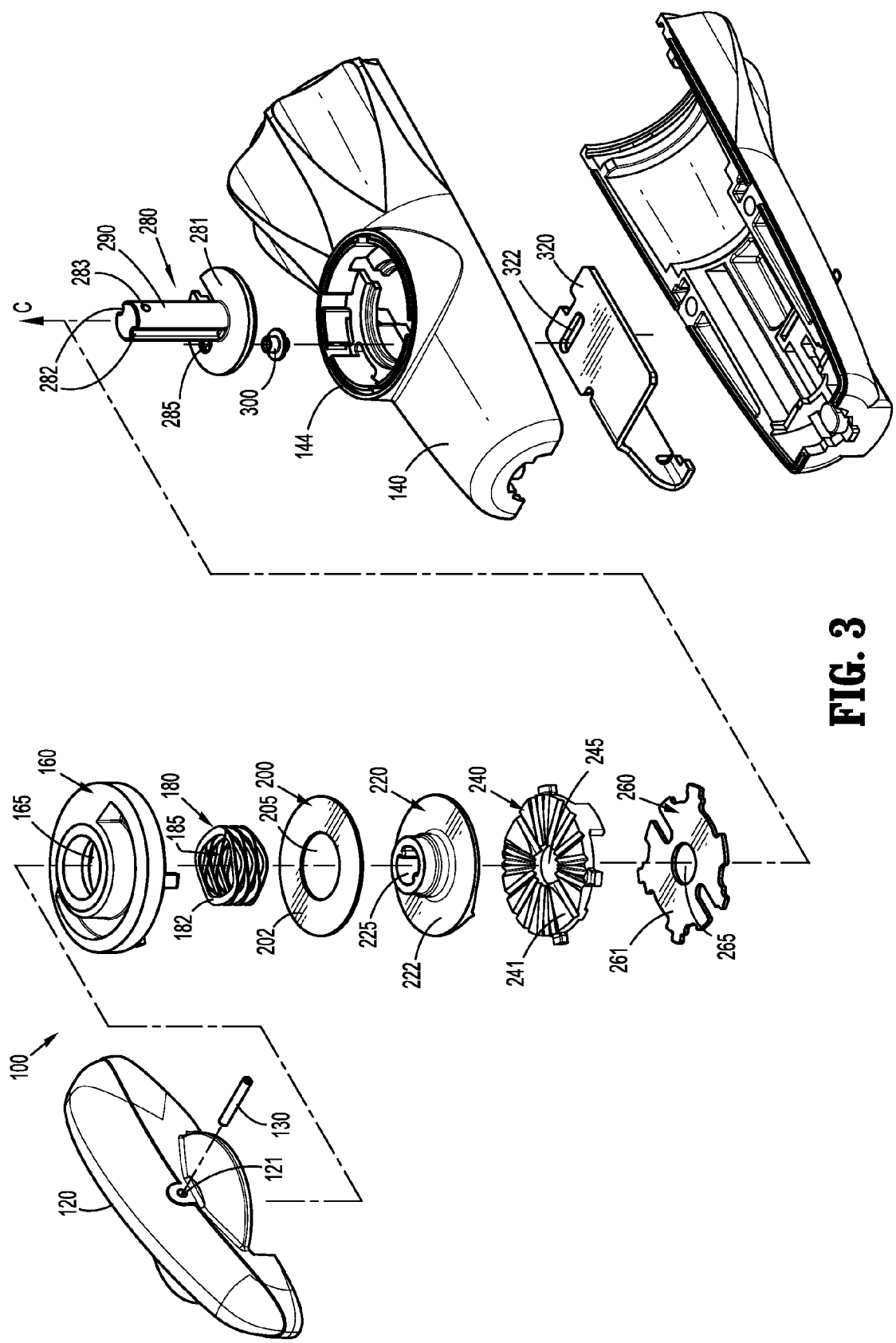
FIG. 3 is a perspective, assembly view of the articulation mechanism of FIG. 2.

With reference to FIGS. 2-18, articulation mechanism 100 includes a lever 120, a knob 140, a cover 160, a biasing element 180, a washer 200, an upper clutch 220, a lower clutch 240, a plate 260, a drive element 280, a cam pin 300, and a yoke 320 (see FIG. 3). Generally, rotation of lever 120 causes rotation of drive element 280, which causes rotation of cam pin 300, thus causing yoke 320 and articulation shaft 500 to translate longitudinally to articulate the jaw members. See FIGS. 3 and 19-21. (Further details of longitudinal translation of an articulation shaft causes articulation of jaw members are explained in U.S. Pat. No. 6,953,139 to Milliman et al., which has been incorporated by reference herein.)

With particular reference to FIG. 3, an assembly view of articulation mechanism 100 is shown. A hub portion 281 of drive element 280 is positioned in contact with a raised ring 144 portion of knob 140. In the embodiment shown, the knob 140 can be used to rotate the elongated portion 30. However, in other embodiments, a housing is used in place of knob 140. Plate 260 is positioned then positioned in contact with hub portion 281 of a shaft portion 290 of drive element 280 and with raised ring 144 portion of knob 140 (discussed in further detail below) such that a shaft portion 290 of drive element 280 extends through a bore 265 in plate 260. Lower clutch 240 is positioned in mechanical engagement with an upper surface 261 of plate 260, and upper clutch 220 is positioned in mechanical engagement with an upper surface 241 of lower clutch 240. Shaft portion 290 of drive element 280 extends through a bore 245 in lower clutch and through a bore 225 in upper clutch 220. In the illustrated embodiment, washer 200 is positioned in mechanical engagement with an upper surface 222 of upper clutch 220 and around shaft portion 290 of drive element 280. Biasing element 180 is positioned in mechanical engagement with an upper surface 202 of washer and about shaft portion 290 of drive element 280. Cover 160 is positioned in mechanical engagement with an upper surface 182 of biasing element 180 and is positioned such that shaft portion 290 of drive element 280 extends through a bore 165 of cover 160. Further, a pin 130 is inserted through an aperture 121 in lever 120 and through an aperture 283 in drive element 280 for mechanical coupling therebetween.

Additional details of the assembly of engagement of the various components of articulation mechanism 100 are discussed in further detail herein. Knob 140 is securable to handle assembly 20 and/or rotation mechanism 70. Knob 140 includes a raised ring 144 including a plurality of engagement structures. Engagement structures are configured for mechanical engagement with plate 260 and lower clutch 240. Specifically, engagement structures include a plurality of retaining walls 147 disposed around an inner periphery of raised ring 144 for engagement with plate 260, and a plurality of recesses 148 defined within an upper surface 145 of raised ring 144 for engagement with lower clutch 240 (see FIGS. 9-13).

Figure 10:
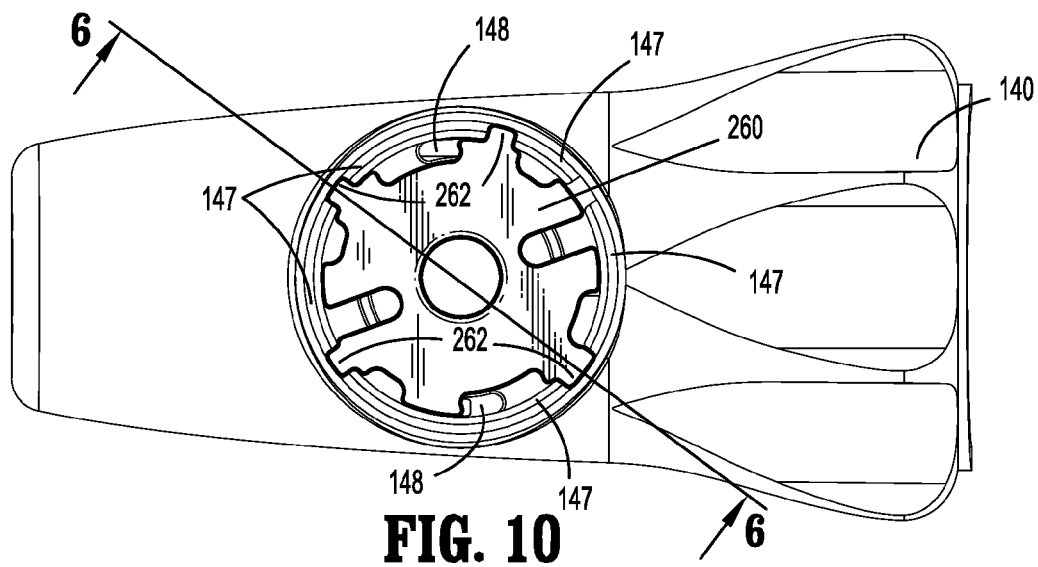
FIGS. 10 and 11 are plan views of the engagement between the plate and the knob of the articulation mechanism of the present disclosure.
Figure 11:
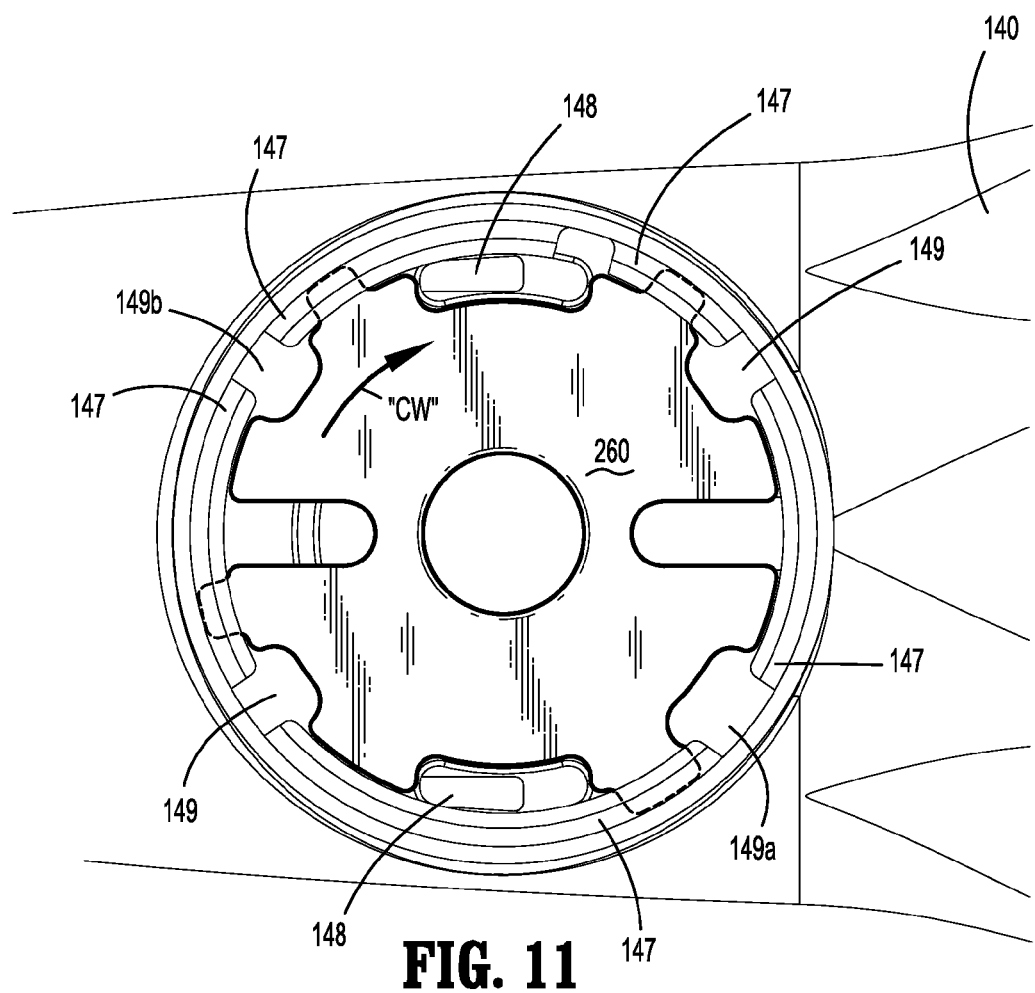
Figure 12:
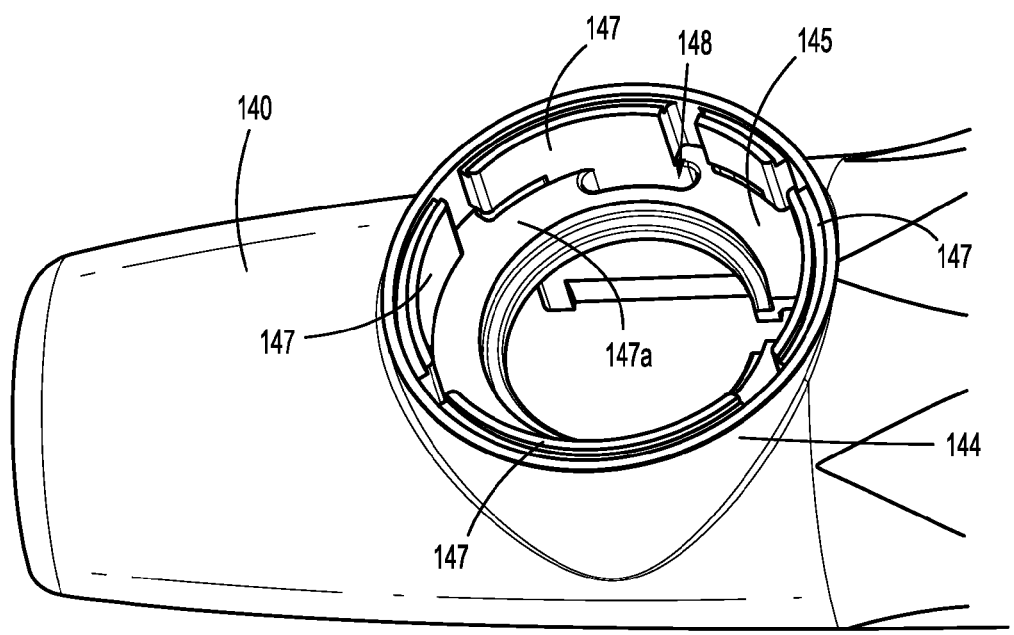
FIG. 12 is a perspective view of a portion of the knob of the articulation mechanism of the present disclosure.
Figure 13:
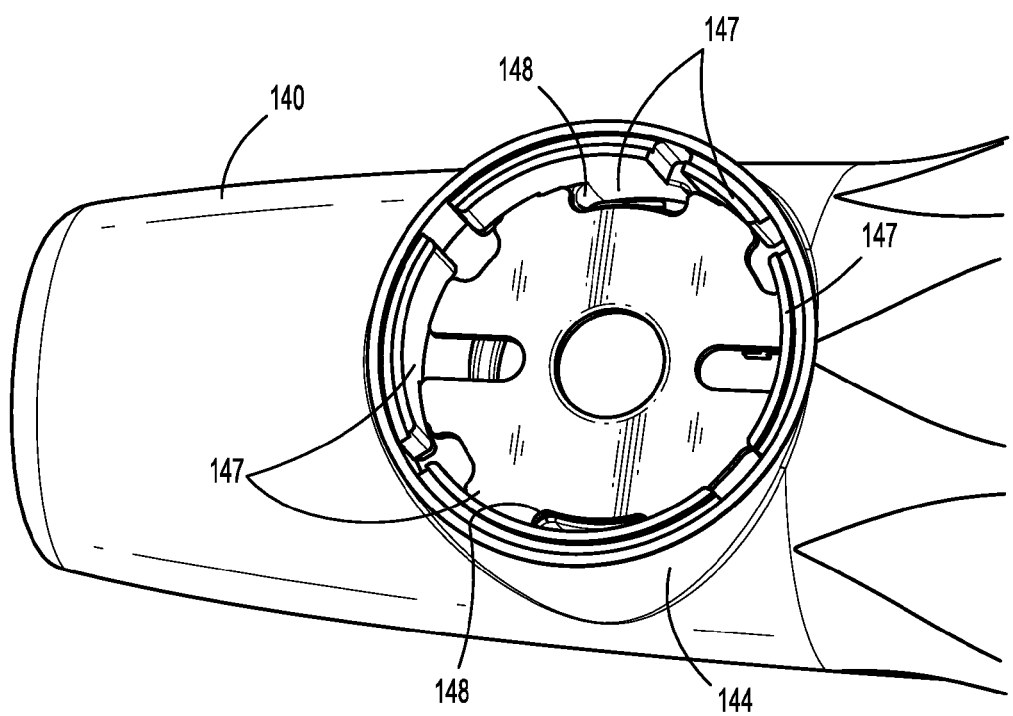
FIG. 13 is a perspective view of the plate engaged with the knob of the articulation mechanism of the present disclosure.

With particular reference to FIGS. 10 and 11, the engagement between plate 260 and knob 140 is illustrated. Plate 260 includes a plurality of first keys 262 configured for engagement with retaining walls 147 of knob 140 (while four first keys 262 are illustrated, plate 260 may include more or fewer than four first keys 262). In particular, plate 260 is initially positioned within raised ring 144 such that first keys 262 are disposed adjacent retaining walls 147. See FIG. 10. Next, plate 260 is rotated (e.g., in a clockwise direction (arrow "CW" FIG. 11)) such that first keys 262 travel at least partially within undercut portions 147a of respective retaining walls 147. See FIGS. 11-13. It is envisioned that plate 260 is rotated until further rotation is physically blocked by contact made between various portions of plate 260 and knob 140 (e.g., see FIGS. 11 and 13). As can be appreciated, the engagement between first keys 262 of plate and retaining walls 147 of knob 140 prevents or limits the movement of plate 260 with respect to knob 140 along a longitudinal axis "C" as defined through drive element 280 (see FIG. 3).

Figure 8:
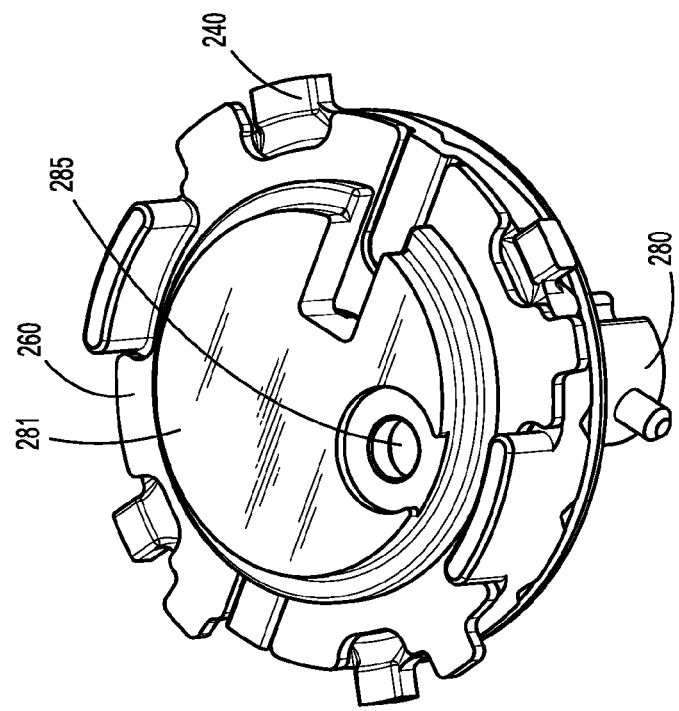
FIG. 8 is a perspective, assembled view of the plate, lower clutch and a shaft of the articulation mechanism of the present disclosure.
Figure 7:
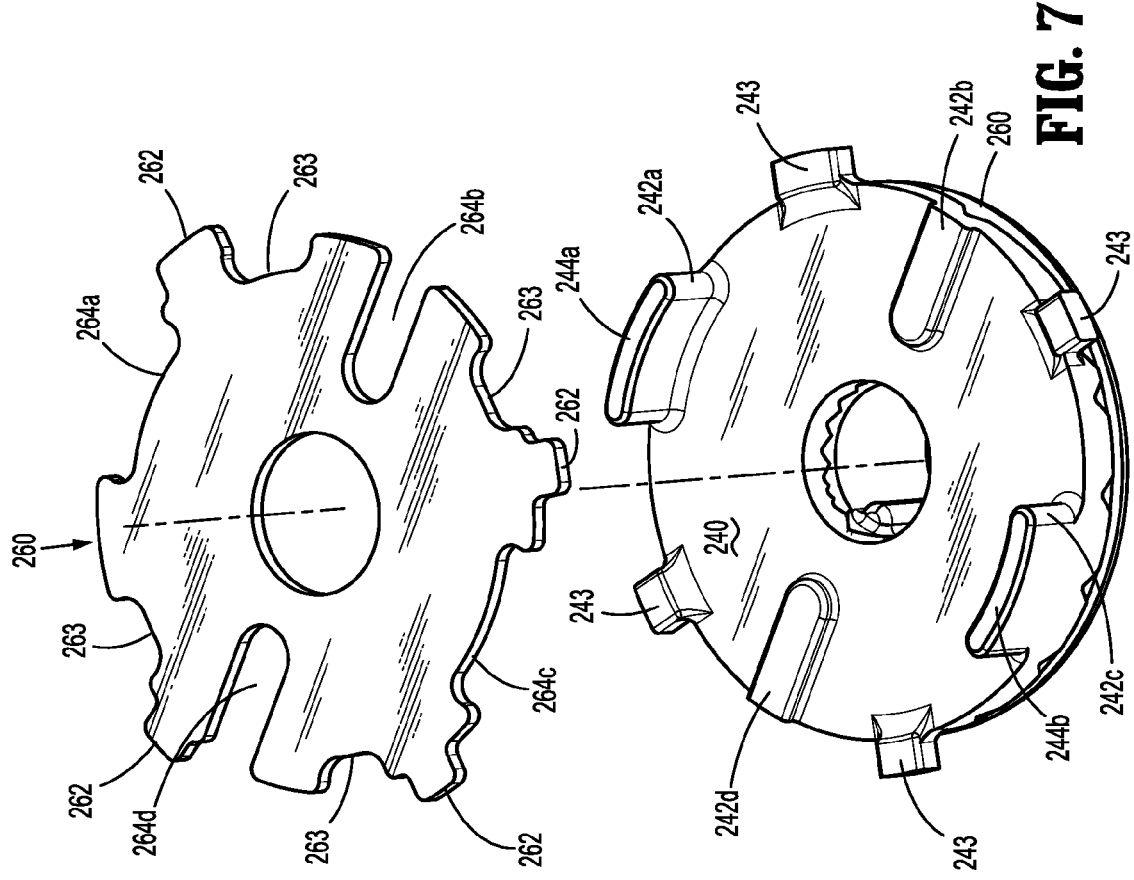
FIG. 7 is a perspective, assembly view of a plate and a lower clutch of the articulation mechanism of the present disclosure.
Figure 9:
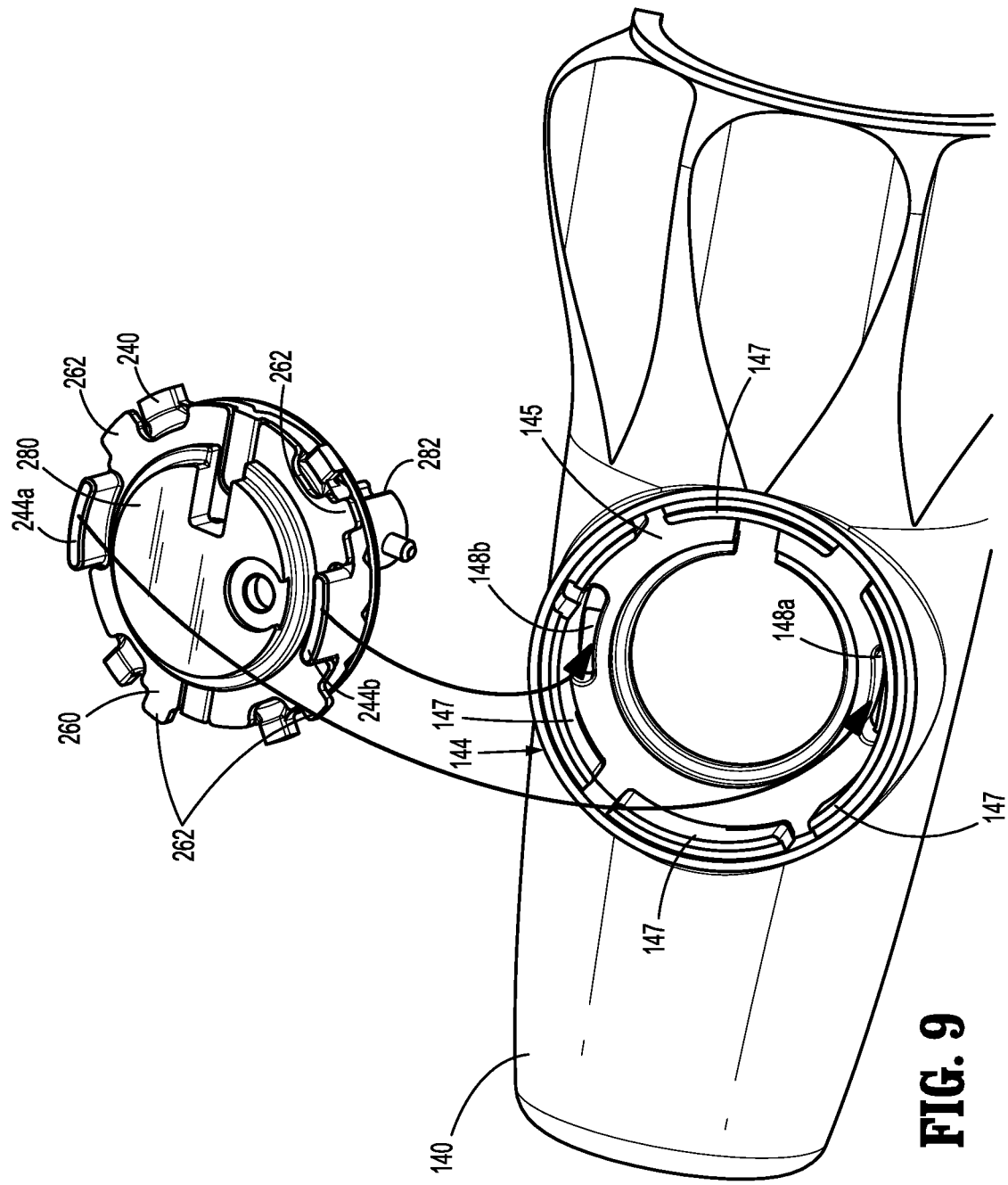
FIG. 9 is a perspective, assembly view including the assembly of FIG. 8 and a knob of the articulation mechanism of the present disclosure.

With reference to FIGS. 7-9, the engagement between plate 260 and lower clutch 240, and the engagement between lower clutch 240 and knob 140 are shown. Lower clutch 240 includes a plurality of first keys 242 configured for mechanically engaging a corresponding set of second keys 264 of plate 260, and lower clutch 240 includes a plurality of second keys 244 configured for mechanically engaging recesses 148 of knob 140. With specific reference to FIGS. 7 and 8, the illustrated embodiment of lower clutch 240 includes four first keys 242a-d configured to mechanically engage four corresponding second keys 264a-d of plate 260. Additionally, the illustrated embodiment of lower clutch 240 includes two second keys 244a-b (second key 244a is part of the same structure as first key 242a, and second key 244b is part of the same structure as first key 242e) configured to mechanically engage two corresponding recesses 148a-b of knob 140. It is envisioned that, first keys 242 and second keys 244 are symmetrically disposed about lower clutch 240. Here, the symmetrical orientation of keys 242 and/or 244 help ensure proper radial orientation between lower clutch 240 and knob 140 (i.e., lower clutch 240 can properly be oriented in two positions with respect to knob 140, with each position being 180° radially offset from each other). It is also envisioned that lower clutch 240 and/or plate 260 include one key that is wider than the others, and that is configured to engage a corresponding wide recess 148 of knob 140. In this embodiment, lower clutch 240 and/or plate 260 are properly engagable with knob 140 is a single orientation.

Alignment projections 243 of lower clutch 240 are configured to engage alignment recesses 149 of knob 140 (see FIGS. 11 and 14), thus preventing rotation therebetween, and facilitating assembly of articulation mechanism 100. Further, plate 260 includes a plurality of radial recesses 263, each of which allow a corresponding alignment projection 243 to extend past plate 260 (or to be substantially aligned with plate 260 along longitudinal axis "C" (see FIG. 3)) and into engagement with knob 140.

Additionally, while FIGS. 7-9 illustrate the engagement between lower clutch 240 and plate 260 prior to plate 260 being engaged with knob 140, it should be appreciated that, in disclosed embodiments, plate 260 is engaged with knob 140 (e.g., plate 260 is rotated with respect to knob 140, as discussed above), prior to engagement between lower clutch 240 and plate 260. As can be appreciated, engagement between first keys 242a-h of lower clutch 240 and second keys 264a-h of plate 260 prevents or substantially prevents rotation between lower clutch 240 and plate 260. Additionally, engagement between second keys 244a-b of lower clutch 240 and recesses 148a-b of knob 140 substantially prevents rotation between lower clutch 240 and knob 140.

Figure 14:
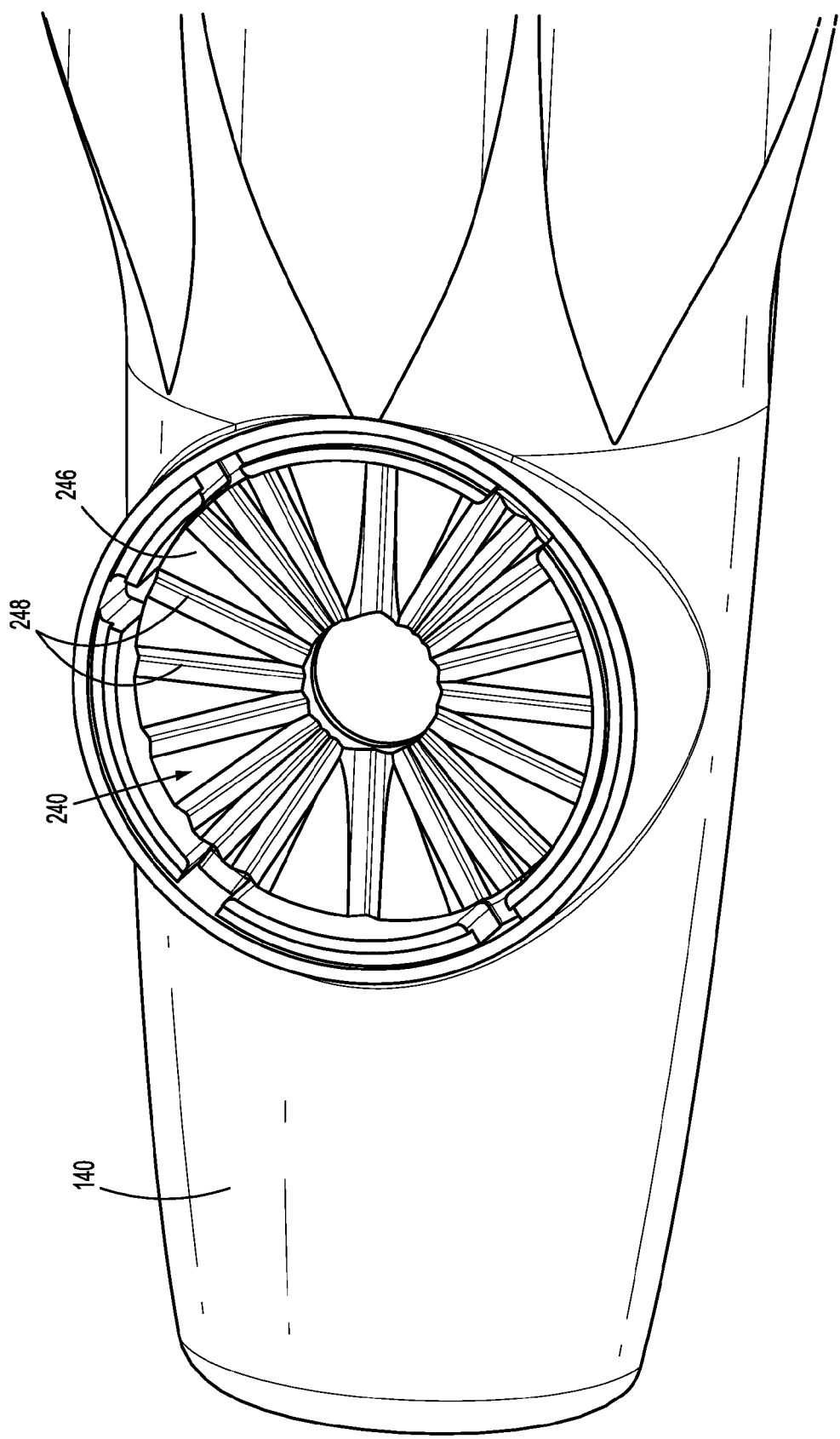
FIG. 14 is a perspective view of the lower clutch engaged with the knob of the articulation mechanism of the present disclosure.

Referring now to FIG. 14, an upper portion 246 of lower clutch 240 including a plurality of serrations 248 is shown. These serrations 248 include angled walls and function to retain articulation lever 120 at a plurality of different articulated positions as will be discussed in further detail below.

Figure 15:
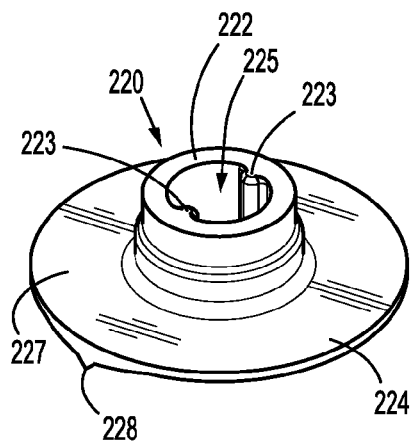
FIGS. 15 and 16 are perspective views of an upper clutch of the articulation mechanism of the present disclosure.
Figure 16:
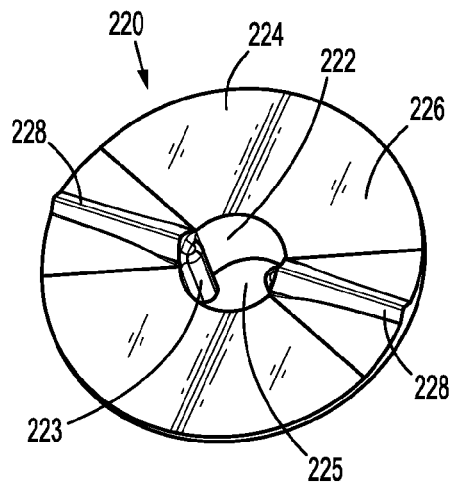

Referring to FIGS. 15 and 16, upper clutch 220 includes a hub portion 222 and a base portion 224. Hub 222 includes fingers 223 extending along and adjacent bore 225. Fingers 223 are configured and dimensioned to mechanically engage slots 282 (see FIGS. 3 and 9) of drive element 280 to rotatably fix upper clutch 240 to drive element 280. Further, the engagement between fingers 223 and slots 282 allow upper clutch 240 to move axially in relation to axis "C" defined by drive element 280 (e.g., in response to force created by biasing element 180 and contact by lower clutch 240). Hub 222 is further configured to extend through bore 205 of washer 200 and at least partially through a central opening 185 of biasing element 180.

Base portion 224 of upper clutch 220 includes an upper face 227 and a lower face 226 (see FIGS. 15 and 16). Lower face 226 of upper clutch 220 is positioned in juxtaposed alignment with serrations 248 of lower clutch 240. Lower face 226 includes a plurality of spaced projections 228 configured to be received within serrations 248 of lower clutch 240. As can be appreciated, engagement between projections 228 of upper clutch 220 and serrations 248 of lower clutch 240 help releasably secure the rotational position of lever 120 with respect to knob 140 (lever is pinned to drive element 280, and drive element 280 is keyed to upper clutch 220 via the engagement between slots 282 and fingers 223, as discussed above), to thereby releasably secure tool assembly 40 at a fixed angle of articulation. Additionally, biasing element 180 is positioned to bias upper clutch 220 towards lower clutch 240. The engagement between biasing element 180 and cover 160 and/or lever 120 provides the force in the opposite direction. Further details of the structures of upper clutch 220 and lower clutch 240, and engagement therebetween, are described in commonly-owned U.S. Pat. No. 8,061,576 to Kenneth Cappola, the entire contents of which are hereby incorporated by reference herein. Further, washer 200 is shown disposed between upper clutch 220 and biasing element 180 to add strength and robustness to articulation mechanism 100, for example.

Figure 17:
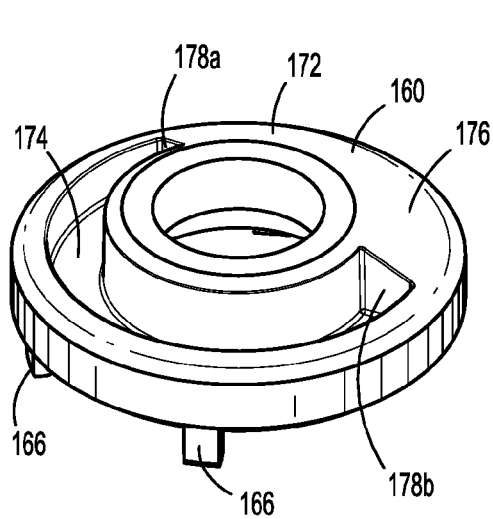
FIGS. 17 and 18 are perspective views of a cover of the articulation mechanism of the present disclosure.
Figure 18:
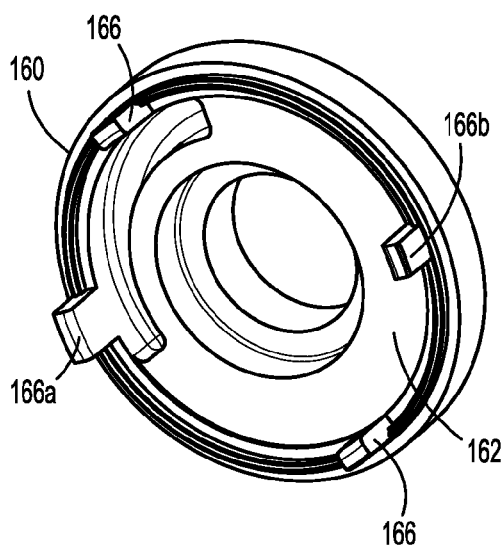

With reference to FIGS. 17 and 18, cover 160 is generally ring-shaped and includes a first (e.g., ventral) side 162 and a second (e.g., dorsal) side 172. First side 162 (FIG. 18) includes a plurality of alignment projections 166. Alignment projections 166 are configured to engage alignment recesses 149 of knob 140 (see FIG. 11), thus preventing rotation therebetween, and facilitating assembly of articulation mechanism 100. Additionally, it is envisioned that a first alignment projection 166a is a different size from a second alignment projection 166b, and it is envisioned that a first alignment recess 149a is a different size from a second alignment recess 149b. In such an embodiment, first alignment projection 166a is configured to engage first alignment recess 149a, and second alignment projection 166b is configured to engage second alignment recess 149b. The different sizes of the alignment features would ensure that cover 160 is properly positioned and radially oriented with respect to knob 140. Further, it is envisioned that cover 160 is attached to knob 140 via at least one weld "W" (see FIG. 5).

Second side 172 of cover 160 includes an arcuate, recessed track 174 extending partially around a surface 176 thereof. In the illustrated embodiment, track 174 extends through second side 172 of cover 160 to first side 162. Track 174 includes a pair of stops 178a, 178b at the ends thereof, and thus forms a C-like shape. Recessed track 174 is mechanically engaged by a key 122 of lever 120 (see FIG. 4).

Figure 4:
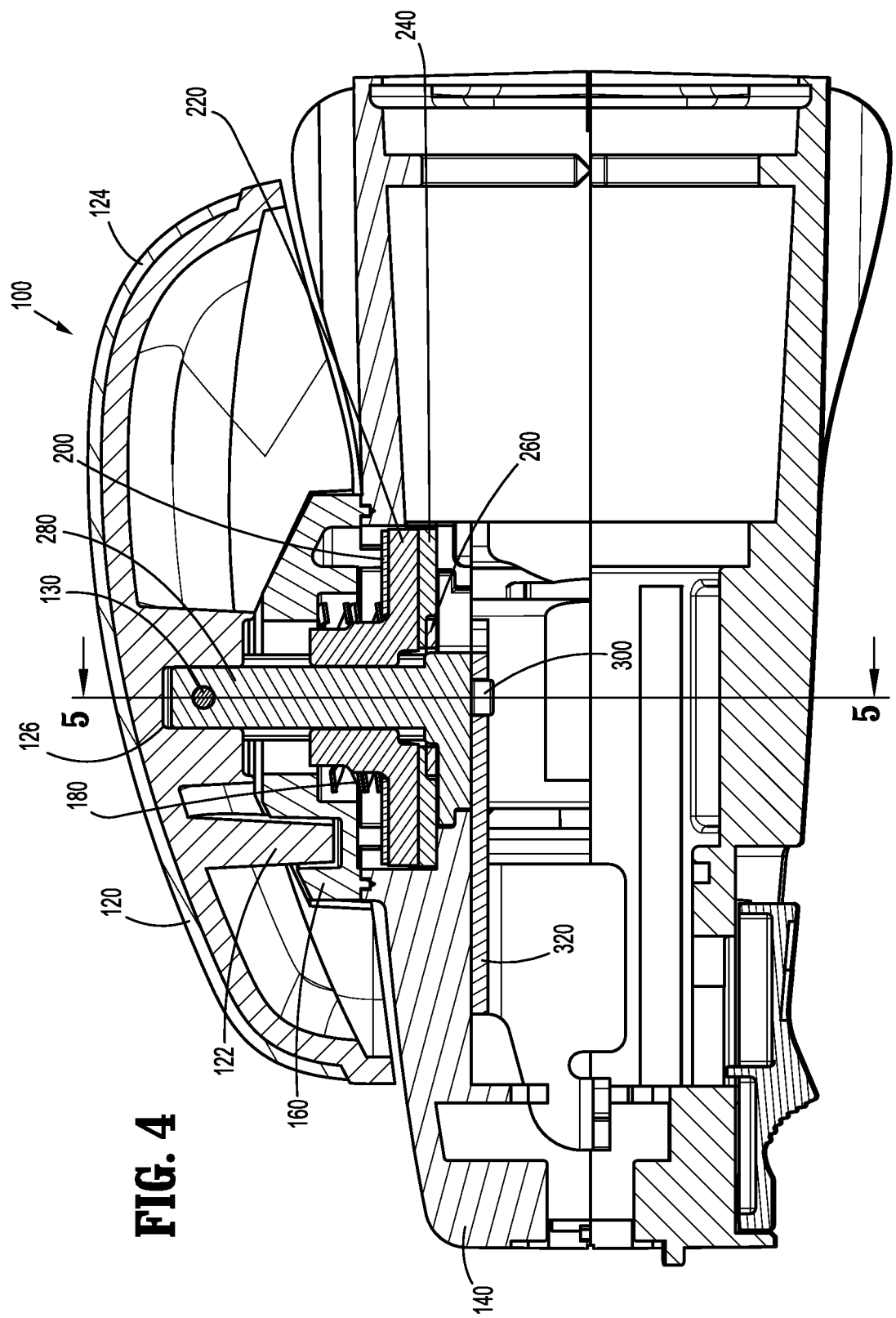
FIG. 4 is a longitudinal cross-sectional view of the articulation mechanism taken along line 4-4 of FIG. 2.

With reference to FIG. 4, lever 120 is shown. Lever 120 includes key 122, a hand-actuatable portion 124, and a recess 126. Key 122 includes an arcuate shape and is configured to follow arcuate track 174 of cover 160. The arcuate length of key 122 is smaller than the arcuate length of track 174, thus allowing lever 120 to rotate with respect to cover 160. Further, key 122 is configured to rotate within track 174 until lateral edges of first key 122 contact respective stops 178a and 178b of track 174, thus preventing further rotational movement. Recess 126 is configured for engaging shaft portion 290 of drive element 280. It is envisioned that recess 126 includes a keyed surface for engaging slots 282 of drive element 280.

With reference to FIGS. 13 and 19-21, cam pin 300 and yoke 320 are shown. Cam pin 300 is engagable with aperture 285 of drive element 280 and depends downwardly therefrom. As shown, aperture 285, and thus cam pin 300, is offset from a radial center of drive element 280 (i.e., aperture 285 is radially off-set from axis "C"). Yoke 320 is disposed in mechanical cooperation with cam pin 300. More particularly, yoke 320 includes a slot 322 therein, which is configured to slidably receive a portion of cam pin 300 therein. Additionally, a distal portion of yoke 320 is disposed in mechanical cooperation with a proximal portion of articulation shaft 500 (see FIGS. 19-21). Further, yoke 320 is rotationally fixed with respect to knob 140 and is longitudinally translatable with respect to knob 140.

In use, to cause articulation of end effector 40, a user rotates lever 120. As lever 120 is rotated, drive element 280, which is pinned and keyed to lever 120, also rotates. Rotation of drive element 280 causes rotation of upper clutch 220, due to the mechanical engagement therebetween, as discussed above. As can be appreciated, the engagement between upper clutch 220, lower clutch 240, and biasing element 180, allows for a controlled rotation of upper clutch 220, and thus drive element 280. Further, rotation of drive element 280 causes cam pin 300 to rotate about axis "C," and to travel within slot 322 of yoke 320, thus causing yoke 320 to translate longitudinally along axis "A." Longitudinal translation of yoke 320 causes articulation shaft 500 to translate longitudinally along axis "A," which articulates the jaw members. See FIGS. 19-21. Moreover, rotation of lever 120 in a first direction (e.g., clockwise), causes drive element 280 and cam pin 300 to rotate in the same (e.g., clockwise) direction about axis "C," which causes yoke 320 to move in a first longitudinal direction along axis "A" (e.g., proximally), which causes the jaw members to articulate in a first direction (e.g., clockwise). Likewise, rotation of lever 120 in a second direction (e.g., counter-clockwise), causes drive element 280 and cam pin 300 to rotate in the same (e.g., counter-clockwise) direction about axis "C," which causes yoke to move in a second longitudinal direction along axis "A" (e.g., distally), which causes the jaw member s to articulate in a second direction (e.g., counter-clockwise).

Figure 5:
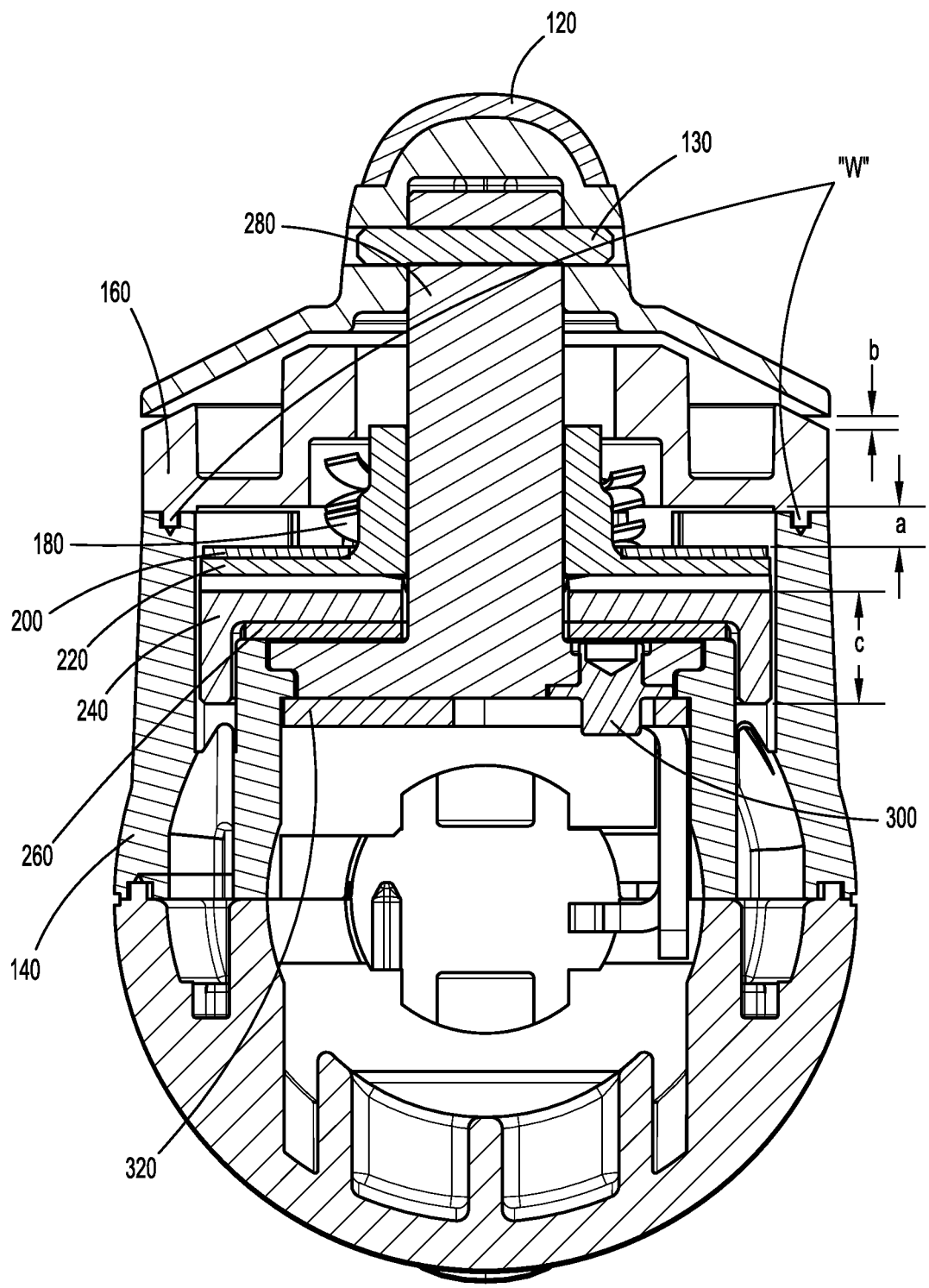
FIG. 5 is a transverse cross-sectional view of the articulation mechanism taken along line 5-5 of FIG. 4.
Figure 6:
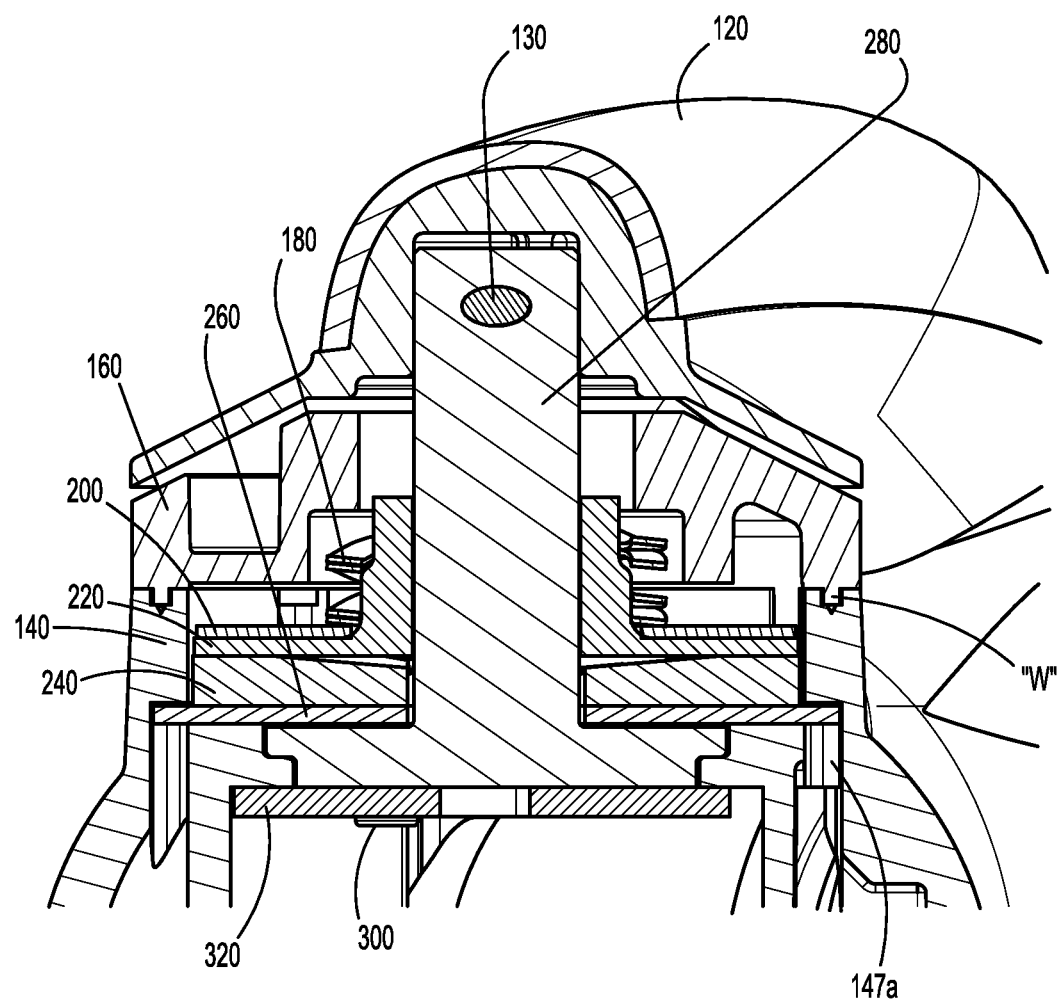
FIG. 6 is a cross-sectional view of a portion of the articulation mechanism taken along line 6-6 of FIG. 10.

As discussed above, cover 160 may be attached to knob 140 via welds "W" (FIG. 5). The present disclosure includes features to help ensure articulation mechanism 100 is still usable even if the weld "W" connection between cover 160 and knob 140 fails. With particular reference to FIG. 5, various distances are illustrated. Distance "a" indicates the distance upper clutch 220 can move with respect to knob 140. Distance "b" indicates the distance cover 160 can move with respect to knob 140 if weld "W" fails (i.e. cover 160 can move until a radial edge thereof contacts lever 120, which is pinned to drive element 280). Distance "c" is the length of second keys 244 of lower clutch 240, which engage recesses 148 of knob 140. In the illustrated embodiment distance "c" is greater than the combined distances "a" and "b." Thus, in situations where weld "W" fails, lower clutch 240 may move away from knob 140 up to a distance "a" plus "b," but since the length of second keys 244 (i.e., distance "c") is greater than distance "a" plus "b," lower clutch 240 maintains engagement (and remains radially fixed) with knob 140. Accordingly, in such situations where weld "W" fails, rotation of lever 120 is still able to cause rotation of drive element 280 and upper clutch 220 with respect to lower clutch 240, to articulate loading unit 40. It is envisioned that distance "a" is between about 0.06 inches and about 0.12 inches. It is envisioned that distance "b" is between about 0 inches and about 0.05 inches in an embodiment. It is envisioned that distance "c" is between about 0.22 inches and about 0.23 inches in an embodiment.

The present disclosure also relates to methods of using and assembling the described surgical instrument 10 or articulation mechanism 100, as discussed above, to perform a surgical procedure, and/or to articulate jaw members of a surgical instrument.

While the above description contains many specifics, these specifics should not be construed as limitations on the scope of the present disclosure, but merely as illustrations of various embodiments thereof. For example, it is envisioned that articulation mechanism 100 is rotatable about the longitudinal axis A-A defined by endoscopic portion 30, such that rotation of articulation mechanism 100 causes rotation of the jaw members. Therefore, the above description should not be construed as limiting, but merely as exemplifications of various embodiments. Those skilled in the art will envision other modifications within the scope and spirit of the claims appended hereto.

The invention claimed is:

1. A surgical instrument for surgically joining tissue, the surgical instrument comprising:
   a handle assembly;
   an elongated portion extending distally from the handle assembly and defining a first longitudinal axis;
   an end effector disposed adjacent a distal portion of the elongated portion, the end effector defining a second longitudinal axis; and
   an articulation mechanism disposed in mechanical cooperation with the end effector for moving the end effector between a first position where the first longitudinal axis is aligned with the second longitudinal axis and a second position where the first longitudinal axis is disposed at an angle with respect to the second longitudinal axis, the articulation mechanism comprising:
      a lever;
      a housing;
      a plate disposed at least partially within a portion of the housing; and
      a lower clutch disposed in mechanical engagement with the plate and movable with respect to the plate,
      wherein at least a portion of the plate is disposed between the lower clutch and at least a portion of the housing, wherein the lower clutch is keyed to the plate via four keys to limit rotation therebetween, and wherein the lower clutch is keyed to the housing to limit rotation therebetween.

2. The surgical instrument of claim 1, wherein the plate is rotatable with respect to the housing.

3. The surgical instrument of claim 1, wherein the lower clutch is keyed to the housing via two keys.

4. The surgical instrument of claim 3, wherein the two keys used to key the lower clutch to the housing are also used to key the lower clutch to the plate.

5. The surgical instrument of claim 1, further comprising a cover disposed in contact with the lever, a biasing element disposed in mechanical cooperation with the cover, and an upper clutch disposed in mechanical cooperation with the lower clutch and in mechanical cooperation with the biasing element.

6. The surgical instrument of claim 5, where the articulation mechanism further includes a knob disposed in mechanical engagement with the lower clutch, wherein a distance the upper clutch can move with respect to the knob is a distance "a," wherein a radial edge of the cover is spaced from the lever a distance "b," wherein the lower clutch is keyed to the housing via at least one key, the at least one key having a distance "c" disposed in the same direction as the distances "a" and "b," and wherein the distance "c" is greater than the distance "a" plus the distance "b".

7. The surgical instrument of claim 5, further comprising a drive element disposed in mechanical cooperation with the housing, a shaft of the drive element extends through an aperture of the plate and through an aperture of the lower clutch, the shaft is mechanically coupled to the upper clutch and the lever.

8. The surgical instrument of claim 7, further comprising an articulation shaft disposed in mechanical cooperation with the drive element, such that rotation of the drive element causes longitudinal translation of the articulation shaft.

9. An articulation mechanism for use with a surgical instrument, the articulation mechanism comprising:
   a lever;
   a knob;
   a lower clutch disposed in mechanical engagement with the knob;
   a cover disposed in contact with the lever;
   a biasing element disposed in mechanical cooperation with the cover; and
   an upper clutch disposed in mechanical cooperation with the lower clutch and in mechanical cooperation with the biasing element;
   wherein a distance the upper clutch can move with respect to the knob is a distance "a," wherein a radial edge of the cover is spaced from the lever a distance "b," wherein the lower clutch is keyed to the knob via at least one key, the at least one key having a distance "c" disposed in the same direction as the distances "a" and "b," and wherein the distance "c" is greater than the distance "a" plus the distance "b".

10. The articulation mechanism of claim 9, further comprising a plate disposed between at least a portion of the knob and at least a portion of the lower clutch.

11. The articulation mechanism of claim 10, wherein the lower clutch is keyed to the plate to limit rotation therebetween.

12. The articulation mechanism of claim 10, wherein the plate is rotatable with respect to the knob.

13. The articulation mechanism of claim 10, wherein the lower clutch is keyed to the plate via four keys.

14. The articulation mechanism of claim 9, wherein the lower clutch is keyed to the knob via two keys.

15. The articulation mechanism of claim 14, further comprising a plate, at least a portion of the plate is disposed between at least a portion of the knob and at least a portion of the lower clutch, wherein the two keys used to key the lower clutch to the knob are also used to key the lower clutch to the plate.

16. The articulation mechanism of claim 9, further comprising a drive element disposed in mechanical cooperation with the knob, a shaft of the drive element extends through an aperture of the plate, and the shaft being mechanically coupled to the lever.

17. The articulation mechanism of claim 16, further comprising an articulation shaft disposed in mechanical cooperation with the drive element, wherein rotation of the drive element causes longitudinal translation of the articulation shaft.

18. An articulation mechanism for use with a surgical instrument, the articulation mechanism comprising:
   a housing;
   a lower clutch; and
   a plate disposed between at least a portion of the lower clutch and a portion of the housing, the plate being movable with respect to the lower clutch,
   wherein the lower clutch is keyed to the plate to limit rotation therebetween, and wherein the lower clutch is keyed to the housing to limit rotation therebetween.

19. A surgical instrument for surgically joining tissue, the surgical instrument comprising:
   a handle assembly;
   an elongated portion extending distally from the handle assembly and defining a first longitudinal axis;
   an end effector disposed adjacent a distal portion of the elongated portion, the end effector defining a second longitudinal axis; and
   an articulation mechanism disposed in mechanical cooperation with the end effector for moving the end effector between a first position where the first longitudinal axis is aligned with the second longitudinal axis and a second position where the first longitudinal axis is disposed at an angle with respect to the second longitudinal axis, the articulation mechanism comprising:
   a lever;
   a housing;
   a plate disposed at least partially within a portion of the housing; and
   a lower clutch disposed in mechanical engagement with the plate and movable with respect to the plate,
   wherein at least a portion of the plate is disposed between the lower clutch and at least a portion of the housing, wherein the lower clutch is keyed to the plate to limit rotation therebetween, and wherein the lower clutch is keyed to the housing via two keys to limit rotation therebetween.

20. The surgical instrument of claim 19, wherein the two keys used to key the lower clutch to the housing are also used to key the lower clutch to the plate.

* * * * *